US009925224B2

(12) United States Patent
Mogna et al.

(10) Patent No.: US 9,925,224 B2
(45) Date of Patent: Mar. 27, 2018

(54) BACTERIAL STRAINS BELONGING TO THE GENUS *BIFIDOBACTERIUM* FOR USE IN THE TREATMENT OF HYPERCHOLESTEROLAEMIA

(75) Inventors: Giovanni Mogna, Novara (IT); Gian Paolo Strozzi, Novara (IT); Luca Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 14/117,003

(22) PCT Filed: May 9, 2012

(86) PCT No.: PCT/IB2012/000907
§ 371 (c)(1),
(2), (4) Date: Dec. 27, 2013

(87) PCT Pub. No.: WO2012/153179
PCT Pub. Date: Nov. 15, 2012

(65) Prior Publication Data
US 2014/0127164 A1 May 8, 2014

(30) Foreign Application Priority Data
May 9, 2011 (IT) .............................. MI2011A0792

(51) Int. Cl.
*A01N 63/00* (2006.01)
*A61K 35/745* (2015.01)
*A23L 29/25* (2016.01)
*A23L 33/105* (2016.01)
*A23L 33/135* (2016.01)
*A23L 33/21* (2016.01)

(52) U.S. Cl.
CPC ............ *A61K 35/745* (2013.01); *A23L 29/25* (2016.08); *A23L 33/105* (2016.08); *A23L 33/135* (2016.08); *A23L 33/21* (2016.08)

(58) Field of Classification Search
CPC ........................... A61K 35/745; A23L 33/135
See application file for complete search history.

(56) References Cited

U.S. PATENT DOCUMENTS

| | | | |
|---|---|---|---|
| 3,819,838 | A | 6/1974 | Lambrou et al. |
| 4,187,321 | A * | 2/1980 | Mutai et al. ................ 426/43 |
| 4,332,790 | A | 6/1982 | Sozzi et al. |
| 4,670,272 | A | 6/1987 | Chen et al. |
| 4,853,211 | A | 8/1989 | Kurobe et al. |
| 5,071,976 | A | 12/1991 | Stirling |
| 6,262,019 | B1 | 7/2001 | Keller et al. |
| 8,257,693 | B2 | 9/2012 | Ranganathan |
| 9,005,682 | B2 | 4/2015 | Sprenger et al. |
| 2002/0022019 | A1 | 2/2002 | Laulund |
| 2002/0044968 | A1 | 4/2002 | Van Lengerich |
| 2004/0185032 | A1 | 9/2004 | Burrell |
| 2004/0208863 | A1 | 10/2004 | Versalovic et al. |
| 2005/0095232 | A1 | 5/2005 | Volkmann |
| 2006/0039973 | A1 | 2/2006 | Aldritt et al. |
| 2006/0121571 | A1 | 6/2006 | Klaenhammer |
| 2006/0233774 | A1 | 10/2006 | Lim et al. |
| 2007/0122397 | A1 | 5/2007 | Sanguansri et al. |
| 2007/0148149 | A1 | 6/2007 | Boettner et al. |
| 2007/0207132 | A1 | 9/2007 | Speelmans et al. |
| 2007/0269515 | A1 | 11/2007 | Henriksen et al. |
| 2008/0175899 | A1 | 7/2008 | Ross et al. |
| 2008/0187628 | A1 | 8/2008 | Champion et al. |
| 2008/0193485 | A1 | 8/2008 | Gorbach et al. |
| 2009/0170185 | A1 | 7/2009 | Hayakawa et al. |
| 2009/0175843 | A1 | 7/2009 | Gans |
| 2009/0252709 | A1 | 10/2009 | Nose et al. |
| 2010/0092440 | A1 | 4/2010 | Strozzi et al. |
| 2011/0177198 | A1 | 7/2011 | Songisepp et al. |
| 2011/0178488 | A1 | 7/2011 | Balazs |
| 2014/0072543 | A1 | 3/2014 | Mogna |

FOREIGN PATENT DOCUMENTS

| | | |
|---|---|---|
| CA | 2221426 | 5/1998 |
| CA | 2739345 | 4/2010 |
| CN | 1345589 A | 4/2002 |
| CN | 1853508 A | 11/2006 |
| CN | 105163747 A | 12/2015 |
| EA | 011952 B1 | 9/2004 |
| EA | 010981 B1 | 2/2007 |
| EP | 0002692 | 7/1979 |
| EP | 0845350 | 11/1996 |
| EP | 0956858 | 11/1999 |
| EP | 1600060 | 11/2005 |

(Continued)

OTHER PUBLICATIONS

Grill et al. Canadian Journal of Microbiology. Oct. 2000, 46, pp. 878-884.*
Klaver et al. Appl Environ Microbiology, 1993, vol. 59, No. 4, pp. 1120-1124.*
PCT International Preliminary Report on Patentability issued on Nov. 12, 2013 for PCT/IB2012/000895 filed on May 9, 2012 in the name of Probiotical S.P.A.
PCT International Preliminary Report on Patentability issued on Nov. 12, 2013 for PCT/IB2012/000897 filed on May 9, 2012 in the name of Probiotical S.P.A.
PCT International Preliminary Report on Patentability issued on Nov. 12, 2013 for PCT/IB2012/000907 filed on May 9, 2012 in the name of Probiotical S.P.A.
Del Piano, M. et al. *Evaluation of the intestinal colonization by microencapsulated probiotic bacteria in comparison with the same uncoated strains.* Journal of Clinical Gastroenterology, vol. 44, pp. S42-S46, Sep. 2010.

(Continued)

*Primary Examiner* — Vera Afremova
(74) *Attorney, Agent, or Firm* — Steinfl + Bruno LLP

(57) ABSTRACT

Selected bacterial strains belonging to the genus *Bifidobacterium* for use in the treatment of hypercholesterolaemia are described. In particular, a food composition or supplement product or medical device or pharmaceutical composition has said bacterial strains in association with sterols or phytosterols and/or stanols or phytostanols and/or glucomannan and/or konjac gum and/or prebiotic fibers and/or fermented red rice and/or betaglucans from oats, oat bran, barley, barley bran and/or *aloe arborescens* gel in lyophilized form.

12 Claims, 3 Drawing Sheets

(56) References Cited

FOREIGN PATENT DOCUMENTS

| | | |
|---|---|---|
| EP | 1600061 | 11/2005 |
| EP | 1840205 A1 | 10/2007 |
| EP | 2 000 530 A1 | 12/2008 |
| EP | 2210505 A1 | 7/2010 |
| EP | 2 269 465 A1 | 1/2011 |
| EP | 2 338 976 A1 | 6/2011 |
| EP | 2360237 A1 | 8/2011 |
| EP | 2 626 076 A1 | 8/2013 |
| JP | 2001-258549 A | 9/2001 |
| JP | 2006-519014 A | 8/2006 |
| JP | 2008-529535 A | 8/2008 |
| JP | 2009-520470 A | 5/2009 |
| JP | 2010-511033 A2 | 4/2010 |
| JP | 2010-187670 A | 9/2010 |
| JP | 2013009681 A | 1/2013 |
| KZ | 11784 A | 8/2002 |
| KZ | 17967 B | 6/2011 |
| RU | 2150268 C1 | 6/2000 |
| RU | 2203946 C1 | 5/2003 |
| RU | 2303058 C2 | 7/2007 |
| RU | 2338511 C2 | 11/2008 |
| RU | 2388479 C1 | 5/2010 |
| WO | 94/12142 | 6/1994 |
| WO | 99/49877 | 10/1999 |
| WO | 00/72855 | 12/2000 |
| WO | 2004/089278 | 10/2004 |
| WO | 2004/101770 | 11/2004 |
| WO | 2006/013588 A1 | 2/2006 |
| WO | 2006/073329 A1 | 7/2006 |
| WO | 2007/029773 A1 | 3/2007 |
| WO | 2007/100765 | 9/2007 |
| WO | 2007/125558 | 11/2007 |
| WO | 2008/038075 | 4/2008 |
| WO | 2008/065492 | 6/2008 |
| WO | 2008/153377 | 12/2008 |
| WO | 2009/138218 | 11/2009 |
| WO | 2010/023248 A1 | 3/2010 |
| WO | 2010/099824 | 9/2010 |
| WO | 2010/103374 | 9/2010 |
| WO | 2010/133761 A1 | 11/2010 |
| WO | 2010133761 A1 | 11/2010 |
| WO | 2011/012932 | 2/2011 |
| WO | 2011/017040 | 2/2011 |
| WO | 2011110918 A1 | 9/2011 |
| WO | 2012/001440 | 1/2012 |
| WO | 2012/101500 A1 | 8/2012 |
| WO | 2010/136891 A1 | 3/2013 |
| WO | 2013/034974 A1 | 3/2013 |
| WO | 2013/034975 A1 | 3/2013 |
| WO | 2013/050831 A1 | 4/2013 |

OTHER PUBLICATIONS

Cheikhyoussef, A. et al. *Antimicrobial activity and partial characterization of bacteriocin-like inhibitory substances (BLIS) produced by Bifidobacterium infantis BCRC 14602.* Food Control, Butterworth, London, GB, vol. 20 (6), pp. 553-559, Jun. 2009.

Kim, J. et al. *Antimicrobial effect of Bifidobacteriumbreve and Bifidobacterium infantis against Salmanella Typhimurium KCTC 1925 and E.coli.* Food Science and Biotechnology, Korean Society of Food Science and Technology, vol. 11 (1), pp. 89-92, Jan. 2002.

Candela, M. et al. *Interaction of probiotic Lactobacillus and Bifidobacteriun strains with human intestinal epithelial cells: Adhesion properties, competition against enteropahtogens and modulation of IL-8 production.* International Journal of Food Microbiology, vol. 125 (3), pp. 286-292, Jul. 2008.

PCT International Search Report mailed on Dec. 16, 2011 for PCT/IB2011/000561 filed on Mar. 17, 2011 in the name of Probiotical S.P.A.

PCT Written Opinion mailed on Dec. 16, 2011for PCT/IB2011/000561 filed on Mar. 17, 2011 in the name of Probiotical S.P.A.

PCT International Preliminary Report on Patentability mailed on Sep. 17, 2013 for PCT/IB2011/000561 filed on Mar. 17, 2011 in the name of Probiotical S.P.A.

Peran, L. et al., *A comparative study of the preventative effects exerted by three probiotics, Bifidobacterium lactis, Lactobacillus casei and Lactobacillus acidophilus, in the TNBS model of rat colitis,* J. Applied Microbiology 2007, 103: 836-844.

Zanoni, S., et al., *Growth kinetics on oligo- and polysaccharides and promising features of three antioxidative potential probiotic strains,* J. Applied Microbiology 2008, 105: 1266-1276.

Lin M., et al., *Antioxidative effect of intestinal bacteria Bifidobacterium longum ATCC 15708 and Lactobacillus acidophilus ATCC 4356,* Digestive Diseases & Sciences 2000, 45: 1617-1622.

Lin, M., et al., *Inhibition fo lipid peroxidation by Lactobacillus acidophilus and Bifidobacterium longum*, J. Agricultural & Food Chemistry 1999, 47: 3661-3664.

PCT International Search Report mailed on Mar. 29, 2012 for PCT/IB2012/000095 filed on Jan. 24, 2012 in the name of Probiotical S.p.A.

PCT Written Opinion mailed on Mar. 29, 2012 for PCT/IB2012/000095 filed on Jan. 24, 2012 in the name of Probiotical S.p.A.

PCT International Preliminary Report on Patentability mailed on Jul. 30, 2013 for PCT/IB2012/000095 on Jan. 24, 2012 in the name of Probiotical S.p.A.

Losada, M et al., *Towards a healthier diet for the colon: the influence of tructooligosaccharides and lactobacilli on intestinal health* Nutrition Research 2002, 22: 71-84.

Italian Search Report and Written Opinion mailed on Nov. 11, 2011 for MI20110792 filed on May 9, 2012 in the name of Probiotical S.p.A.

PCT International Search Report issued for PCT/IB2012/001745 filed on Sep. 10, 2012 in the name of Probiotical S.P.A. mail date: Dec. 17, 2012.

PCT Written Opinion issued for PCT/IB2012/001745 filed on Sep. 10, 2012 in the name of Probiotical S.P.A. mail date: Dec. 17, 2012.

Zhang L et al (2010) "Evaluation of Lactobacilus rhamnosus GG using an *Escherichia coli* K88 model of piglet diarrhoea: Effects on diarrhoea incidence, faecal microflora and immune responses" Veterinary Microbiology. Elsevier BV. NL. vol. 141, No. 1-2, pp. 142-148.

K. A. Eaton et al (2011) "Probiotic Lactobacillus reuteri Ameliorates Disease Due to Enterohermorrhagic *Escherichia coli* in Germfree Mice" Infection and Immunity, vol. 79, No. 1.pp. 185-191.

K. C. Johnson-Henry et al (2008) "Lactobacillus rhamnosus Strain GG Prevents Enterohemorrhagic *Escherichia coli* 0157:H7-induced Changes in Epithelial Barrier Function" Infection and Immunity, vol. 76, No. 4,pp. 1340-1348.

A. Marchese (2003) "Effect of fosfomycin alone and in combination with N-acetylcysteine on *E coli* biofilms" International Journal of Antimicrobial Agents, vol. 22 Suppl 2:95-100.

Collado M. C. et al (2007) "Probiotic Strains and Their Combination Inhibit In Vitro Adhesion of Pathogens to Pig Intestinal Mucosa" Current Microbiology, Springer-Verlag, NE. vol. 55. No. 3, pp. 260-265.

Dan Yang Ying et al (2010) "Microencapsulated Lactobacillus rhamnosus GG Powders: Relationship of Powder Physical Properties to Probiotic Survival during Storage," Journal of Food Science. vol. 75, No. 9.

Champagne C. P. et al (2010) "The determination of viable counts in probiotic cultures microencapsulated by spray-coating." Food Microbiology, Academic Press Ltd. London. GB. vo 1 • 27. No. 8, pp. 1104-1111.

Hutt P et al (2006) "Antagonistic activity of probiotic lactobacilli and bifidobacteria against entero- and uropathogens." Journal of Applied Microbiology, vol. 100. No. 6 pp. 1324-1332.

Gueimonde M et al (2006) "Adhesion and competitive inhibition and displacement of human enteropathogens by selected lactobacilli" Food Research International. Elsevier Applied Science, Barking, GB. vol. 39, No. 4.

McFarland Lynne V (2006) "Meta-analysis of probiotics for the prevention of antibiotic associated diarrhea and the treatment of Clostridium difficile disease." The American Journal of Gastroenterology Apr. 2006 LNKD-Pubmed: 16635227, vol. 101, No. 4 pp. 812-822.

(56) References Cited

OTHER PUBLICATIONS

Rada V et al (2009) "Susceptibility of bifidobacteria to lysozyme as a possible selection criterion for probiotic bifidobacterial strains." Biotechnology Letters, Springer Netherlands, Dordrecht. vol. 32, No. 3, pp. 451-455.
Fernandez M Fetal (2003) "Probiotic properties of human lactobacilli strains to be used in the gastrointestinal tract." Journal of Applied Microbiology, Oxford. GB. vol. 94, No. 3 pp. 449-455.
PCT International Search Report issued for PCT/IB2012/001741 filed on Sep. 10, 2012 in the name of Giovanni Mogna. mail date: Dec. 3, 2012.
PCT Written Opinion issued for PCT/IB2012/001741 filed on Sep. 10, 2012 in the name of Giovanni Mogna. mail date: Dec. 3, 2012.
Lu et al (2007) "New development in the mechanistic understanding of peptic ulcer diseases", Drug Discovery Today: Disease Mechanisms, Elsevier, vol. 3, No. 4, pp. 431-437.
Hien Quoc Huynh et al (2004) "N-Acetylcysteine, a Novel Treatment for Helicobacter pylori infection", Digestive Diseases and Sciences, Kluwer Academic Publishers—Plenum Publishers, NE, vol. 49, No. 11-12 pp. 1853-1861.
Gotteland M et al (2006) "Systematic review: Are probiotics useful in controlling gastric colonizationby Helicobacter pylori?" Alimentary Pharmacology & Therapeutics, Blackwell Scientific Publications Ltd., Cambridge, GB, vol. 23, No. 8 pp. 1077-1086.
Del Piano Mario et al (2011) "Is microencapsulation the future of probiotic preparations? The increased efficacy of gastro-protected probiotics." Gut Microbes 2011 MAR-APR LNKDPUBMED: 21637030, vol. 2, No. 2, pp. 120-123.
PCT international Search Report issued for PCT/IB2012/001848 filed on Sep. 21, 2012 in the name of Giovanni Mogna, mail date: Dec. 3, 2012.
PCT Written Opinion issued for PCT/IB2012/001848 filed on Sep. 21, 2012 in the name of Giovanni Mogna. mail date: Dec. 3, 2012.
Ronnqvist et al. (Lactobacilius fermentum Ess-1 with unique growth inhibition of vulvo vaginal candidas pathogens. Journal of Medical Microbiology (2007), 56, pp. 1500-1504.
Lutgendorff, Fetal, Probiotics enhance pancreatic glutathione biosynthesis and reduce oxidative stress in experimental acute pacreatitis. Am. J. Physiol Gastrointest. Liver Physiol. 2008. 295: G1111-G1121.
Malecka, M. Antioxidant properties of the usaponifiable matter isolated from tomato seeds, oat grains and wheat germ oil, Food Chemistry. 2002, 79 pp. 327-330.
Del Piano et al., "Evaluation of the intestinal colonization by microencapsulated probiotic bacteria in comparison with same uncoated strains." J. Clin. Gastroenterol, 44: S42-S46 (2010).
Grimoud et al., "In vitro screening of probiotic lactic acid bacteria and prebiotic glucooligosaccharides to select effective synbiotics." Anaerobe 16: 493-500 (2010).
Okombo et al., "Probiotic-induced reducetion of gastrointestinal oxalate absorption in healthy subjects." Urol. Res. 201 O: 169-178 (2010).
Marfarlane et al., "Review article: prebiotics in the gastrointestinal tract." Aliment. Pharmacol. Ther. 24: 701-714 (2006).
PCT International Search Report mailed on Sep. 21, 2012 for PCT/IB2012/000895 filed on May 9, 2013 in the name of Probiotical S.P.A.
PCT Written Opinion mailed on Sep. 21, 2012 for PCT/IB2012/000895 filed on May 9, 2013 in the name of Probiotical S.P.A.
PCT International Search Report mailed on Sep. 27, 2012 for PCT/IB2012/000907 filed on May 9, 2013 in the name of Probiotical S.P.A.
PCT Written Opinion mailed on Sep. 27, 2012 for PCT/IB2012/000907 filed on May 9, 2013 in the name of Probiotical S.P.A.
PCT International Search Report mailed on Aug. 24, 2012 for PCT/IB2012/00897 filed on May 9, 2013 in the name of Probiotical S.P.A.
PCT Written Opinion mailed on Aug. 24, 2012 for PCT/IB2012/000897 filed on May 9, 2013 in the name of Probiotical S.P.A.
Modesto, M. et al. *Resistant to freezing and freeze-drying storage processes of potential probiotic bifidobacteria*. Annals of Microbiology, 54(1), pp. 43-48 (2004).
Likotrafiti, E et al *Molecular Identification and Anti-pathogenic Activities of Putative Probiotic Bacteria Isolated from Faeces of Healthy Elderly Idividuals*. Microbial Ecology in Health and Disease. 16, pp. 105-112 (2004).
"7th Probiotics & Prebiotics—new food", Universita Urbaniana, Rome. Poster 66: "Effectiveness of the Two Microorganisms L. Fermentum LF15 and L Plantarum LP01, Formulated in Slow Release Vaginal Tablets, in Women Affected by Bacterial Vaginosis (BV): A Pilot Study", Jul. 2013. 52 pages.
"Sachet" Webpage from merriam-webster.com, Oct. 7, 2011, accessed via WayBackMachine.com. 1 page.
Al-Wahsh, I. et al."Acute probiotic ingestion reduces gastrointestinal oxalate absorption in healthy subjects." Urological Research, vol. 40(3), pp. 191-196. Aug. 2011.
Amaretti, A. et al. *Antioxidant properties of potentially probiotic bacteria: in vitro and in vivo activities*. Applied Microbiology and Biotechnology. vol. 97 (2), 2013, pp. 809-817.
Santini, C. et al., "Characterization of probiotic strains: an application as feed additives in poultry against *Campylobacter jejuni*", Int J Food Microbiol., 2010, 141 Suppl 1:S98-108. Epub 2010 Apr 8. Abstract Only.
Castro-Leyva, V. et al. "Preserved Ex Vivo Inflammatory Status in Decidual Cells from Women with Preterm Labor and Subclinical Intrauterine Infection." Plos One, vol. 7 (8), e43605, pp. 1-6. Aug. 2012.
Pina, et al., "Prevalence and dietetic management of mild gastrointestinal disorders in milk-fed infants", World Journal of Gastroenterology, 2008, vol. 14, No. 2: 248-254.
European Commission—Health & Consumer Protection Directorate-General, "Opinion of the Scientific Committee on Animal Nutrition on the Criteria for Assessing the Safety of Micro-Organisms Resistant to Antibiotics of Human Clinical and Veterinary Importance", 2002, pp. 1-20.
European Patent Office Communication pursuant to Article 94(3) EPC in relation to Application No. 12 780 278.3-1401. Mailed Jun. 12, 2015.
FAO/WHO. *Guidelines for the Evaluation of Probiotics in Food*. Apr. 30/May 1, 2002, 11 pgs.
Hoesl, C. E. et al. "The Probiotic Approach: An Alternative Treatment Option in Urology" European Urology, vol. 47, No. 3, pp. 288-296. Mar. 2005.
International Preliminary Report on Patentability for PCT/IB2012/001745 filed on Sep. 10, 2012 in the name of Probiotical North America Inc. mail date: Mar. 12, 2014.
International Search Report issued for International Application No. PCT/IB2014/000731 filed on May 14, 2014 in the name of Probiotical S.P.A. Mail date: Jul. 25, 2014.
International Search Report issued for International Application No. PCT/IB2014/000739 filed on May 14, 2014 in the name of Probiotical S.P.A. Mail date: Jul. 31, 2014.
Walter, J. et al. "Detection and Identification of Gastrointestinal *Lactobacillus* Species by Using Denaturing Gradient Gel Electrophoresis and Species-Specific PCR Primers", Appl. Environ. Microbiol. 2000. vol. 66 (1), pp. 297-303.
L. Ouoba, et al., "Resistance of potential probiotic lactic acid bacteria and bifidobacteria of African and European origin to antimicrobials: Determination and transferability of the resistance genes to other bacteria", International Journal of Food Microbiology, 2008, 121, 217-224.
Milani, C. et al., "Comparative Genomics of *Bifidobacterium animalis* subsp. lactis Reveals a Strict Monophyletic Bifidobacterial Taxon", Applied and Environmental Microbiology, 79 (14), 2013, 4304-4315.
Mogna, L. et al. "Assessment of the in vitro inhibitory activity of specific probiotic bacteria against different *Escherichia coli* strains." Journal of Clinical Gastroenterology, vol. 46, Supp. 1, pp. S29-S32. Oct. 2012.

(56) References Cited

OTHER PUBLICATIONS

Pascual, L. et al. "Vaginal Colonization and Activity of the Probiotic Bacterium *Lactobacillus Fermentum* L23 in a Murine Model of Vaginal Tract Infection", Journal of Medical Microbiology, vol. 59, No. 3, pp. 360-364, Nov. 2009.
S. Keersmaecker et al. "Strong antimicrobial activity of Lactobacillus rhamnosus GG against *Salmonella typhimurium* is due to accumulation of lactic acid" Federation of European Microbiological Societies Microbiology Letters 259. (2006) 89-96.
Torriani, S. et al. *Differentiation of Lactobacillus plantarum, L. pentosus, and L. paraplantarum by recA Gene Sequence Analysis and Multiplex PCR Assay with recA Gene-Derived Primers*. Appl. Environ. Microbiol. 2001. vol. 67 (8), pp. 3450-3454.
Saggioro, A. "Probiotics in the Treatment of Irritable Bowel Syndrome." Journal of Clinical Gastroenterology, vol. 38(6), pp. S104-106. Jul. 2004.
Strus, M. et al. "Studies on the Effects of Pro Biotic *Lactobacillus* Mixture Given Orally on Vaginal and Rectal Colonization and on Parameters of Vaginal Health in Women with Intermediate Vaginal Flora" Eurpoean Journal of Obstetrics Gynecology and Reproductive Biology, vol. 163, No. 2 pp. 210-215. Aug. 2012.
The EFSA Journal, "Opinion of the Scientific Panel on Additives and Products or Substances used in Animal Feed on the updating of the criteria used in the assessment of bacteria for resistance to antibiotics of human and veterinary importance", 2005, 223, pp. 1-12.
V. Rada, et al. "Susceptibility of bifidobacteria to nisin", Letters in Applied Microbiology, vol. 26, 1998, pp. 123-125.
Vicariotto, F. et al: "65: Effectiveness of an Association of a Cranberry Dried Extract, D-Mannose and the Three Microorganisms L. Plantarum Lp01, L. Paracasei, Lpc09 and S. Thermophilus St10 in Women Affected by Cystitis: A Pilot Study", 7th Probiotics & Prebiotics New Foods, pp. 1-52, Jul. 2013.
Written Opinion issued for International Application No. PCT/IB2014/000731 filed on May 14, 2014 in the name of Probiotical S.P.A. Mail date: Jul. 25, 2014.
Written Opinion issued for International Application No. PCT/IB2014/000739 filed on May 14, 2014 in the name of Probiotical S.P.A. Mail date: Jul. 31, 2014.
International Preliminary Report on Patentability issued for International Application No. PCT/IB2014/000739 filed on May 14, 2014 in the name of Probiotical S.P.A. Mail date: Nov. 26, 2015. 14 pages.
Ouwehand, A. et al. "Probiotics: an Overview of beneficial effects" Antonie van Leeuwenhoek. 2002, vol. 82; pp. 279-289.
Puccio, G. et al. "Clinical evaluation of a new starter formula for infants containing live Bifidobacterium longum BL999 and prebiotics" Nutrition 2007 vol. 23; pp. 1-8.
Alam, M et al. "Development and Evaluation of Acid-buffering Bioadhesive Vaginal Tablet for Mixed Vaginal Infections" AAPS PharmSciTech 2007; vol. 8, No. 4, Article 109. pp. E1-8.
Bordoni, A. et al. "Cholesterol-lowering probiotics: in vitro selection and in vivo testing of bifidobacteria" Applied Microbiology and Biotechnology. Sep. 2013. vol. 97, No. 18 pp. 8273-8281.
Briczinski, E. et al. "Strain-Specific Genotyping of *Bifidobacterium animalis* subsp. lactis by Using Single-Nucleotide Polymorphisms, Insertions, and Deletions" Applied and Environmental Microbiology. Dec. 2009. vol. 75, No. 23, pp. 7501-7508.
Candela, et al. "High taxonomic level fingerprint of the human intestinal microbiota by Ligase Detection Reaction—Universal Array approach" BMC Microbiology; 2010; vol. 10; No. 116; 16 pages.
Cremonini et al. "Effect of Different Probiotic Preparations on Anti-Helicobacter pylori Therapy-Related Side Effects: A Parallel Group, Triple Blind, Placebo-Controlled Study" Am. J. Gastroenterol.; 2002; vol. 97; pp. 2744-2749.
Federici, et al. "Characterization and Heterologous Expression of the Oxalyl Coenzyme A Decarboxylase Gene from Bifidobacterium lactis" Applied and Environmental Microbiology, Sep. 2004; vol. 70; No. 9; pp. 5066-5073.

Guardamagna et al. "Bifidobacteria supplementation: Effects on plasma lipid profiles in dyslipidemic children" Nutrition, 2014; vol. 30; pp. 831-836.
Guo, X. "Basics and Application of Probiotics" Science and Technology Press, 1st Version, Oct. 2002. 2 pages (Chinese Original. English Translation in NPL Reference No. 42).
http://intranet.comunidadandina.org/Documentos/Gacetas/Gace722.PDF Breach Action Filed by the General Secretary of the Andean Community Against the Republic of Peru, Process 89-AI-2000 (Gaceta Oficial, del Acuerdo de Cartagena, Sumario, Tribunal de Justicia de la Comunidad Andina), Ano XVIII, Numero 722, Lima, 12 de octubre 2001, 44 pgs. Spanish with English Abstract.
http://www.ub.es/legmh/capitols/sunyenegre.pdf Dr. Jose Ma Sune NEGRE, New Galenic Formulations to Forms of Administration (Nuevas Aportaciones Galenicas a las Formas de Administracion. En: Curos de formacion continuada para farmaceuticos de hospital. Fundacion Promocion Medica. Barcelona, 2002, 3, pp. 27-65), 3.2. 27 pgs. Spanish with English Abstract.
Kim, H.S. et al. "In vitro Antioxidative Properties of Lactobacilli" Asian-Aust. J. Anim. Sci. 2006; vol. 19; No. 2, pp. 262-265.
Lieske, et al. "Use of a probiotic to decrease enteric hyperoxaluria" Kidney International; 2005; vol. 68; pp. 1244-1249.
Liu, J-R. et al. "Antioxidative Activities of Kefir" Asian-Aust. J. Anim. Sci, 2005; vol. 18. No. 4; pp. 567-573.
Masashi Okamura, "Youkei no Tomo", 2008, vol. 558, pp. 17-21 (Japanese original + English translation).
McFarland, L.V. "Meta-analysis of probiotics for the prevention of antibiotic associated diarrhea and the treatment of Clostridium difficile disease", The American Journal of Gastroenterology Apr. 2006, vol. 101, No. 4, Apr. 2006, pp. 812-822.
Mei, X. et al. "Manual of New Drug and Special Drug" Technology Press, 2nd Version, Jan. 2001. 2 pages.
Shigeru Kamiya, "Igaku no Ayumi" Journal of Clinical and Experimental Medicine, 2003; vol. 207; No. 10, pp. 894-898 (Japanese original + English translation).
Turroni, et al. "Oxalate consumption by lactobacilli: evaluation of oxalyl-CoA decarboxylase and formyl-CoA transferase activity in Lactobacillus acidophilus" Journal of Applied Microbiology; 2007; vol. 103; pp. 1600-1609.
Van Hemert, Et al. "Influence of the Multispecies Probiotic Ecologic Barrier on Parameters of Intestinal Barrier Function" Food and Nutrition Sciences, 2014, 5, pp. 1739-1745.
Wikipedia "Pharmaceutical Drug" Updated Apr. 15, 2016. Downloaded from the internet Apr. 21, 2016. 11 pages.
Wikipedia, "Strain (biology)" https://en.wikipedia.org/wiki/Strain_(biology) Retrieved on Nov. 3, 2015. 2 pgs.
Yoon, Y. et al. "Occurrence of Glutathione Sulphydryl (GSH) and Antioxidant Activities in Probiotic *Lactobacillus* spp." Asian-Aust. J. Anim Sci, 2004; vol. 17; No. 11; pp. 1582-1585.
Yutaka Kanamori, Joumyaku Keichou Eiyou "Parenteral and Enteral Nutrition", 2010, vol. 25; No. 4, pp. 923-928 (Japanese original + English translation).
Notification of the Second Office Action for Chinese Patent Application No. 201280034204.6 filed on behalf of Probiotical S.P.A. dated Oct. 21, 2016. 17 pages (Chinese original + English translation).
Zhang Guonong et al., China; Light Industry Press, first edition in 2009, publication date: Aug. 31, 2009. pp. 363 (Chinese original + English excerpt).
Wu Qingbin, et al., Science Press; first edition, publication date: Jun. 30, 2012. pp. 118-123 (Chinese original + English excerpt).
"DeNol" 2009; found on the internet Mar. 29, 2016; www.rlsnet.ru/tn_index_id_6426.htm; 6 pages (Russian original + English translation of relevant parts).
Bespalov, V.G. et al. "Biologically active food supplements" Kafedra, 2000; pp. 38-47 (Russian original + English translation of relevant parts).
Champagne, et al: "The determination of viable counts in probiotic cultures microencapsulated by spray-coating", Food Microbiology, Academic Press Ltd, London, GB, vol. 27, No. 8, Dec. 1, 2010 (Dec. 1, 2010), pp. 1104-1111. Abstract Only.

(56) References Cited

OTHER PUBLICATIONS

Chilean First Examination report dated Feb. 12, 2016 for Chilean application No. 2013-002148 filed on Jul. 26, 2013 in the name of Probiotical S.P.A., 21 pgs. Spanish with English translation.
Del Piano, M. et al. "Correlation between chronic treatment with Proton Pump Inhibitors (PPIs) and bacterial overgrowth in the stomach: any possible beneficial role for selected lactobacilli?" J. Clin. Gastroenterol., 48 Suppl 1: S40-6. 13 pgs. Nov.-Dec. 2014.
First Office Action for Chinese Patent Application No. 201280022854.9 dated Nov. 4, 2014 filed on May 9, 2012 in the name of Probiotical S.P.A. (English + Chinese). 15 pages.
Germond, J.E. et al. "Evolution of the bacterial species Lactobacillus delbrueckii: a partial genomic study with reflections on prokaryotic concept." Mol. Biol. Evol. vol. 20(10, pp. 93-104. Jan. 2003 (Abstract Only).
Gurbuz et al. "Effect of N-Acetyl Cysteine on Helicobacter pylori" Souther Medical Journal; Nov. 2005; 2002; vol. 97; pp. 2744-2749.
Hamilton-Miller, "The role of probiotics in the treatment and prevention of Helicobacter pylori infection", International Journal of Antimicrobial Agents Oct. 2003 LNKD—PUBMED 14522098, vol. 22, No. 4, Oct. 2003, pp. 360-366, XP002661415.
Karamanolis et al. "A Glass of Water Immediately Increases Gastric pH in Healthy Subjects" Dig. Dis Sci., 2008, vol. 53, pp. 3128-3132.
Khavkin, A.I. et al. "Modern principles of ulcer disease" 2009; found on the internet Mar. 29, 2016; www.lvrach.ru/2005/02/4532114/; 6 pages (Russian original + English translation of relevant parts).
Krosnyuk, I.I. et al. "Pharmaceutical technology: Technology of dosage forms: a textbook for university students" Academia editorial center; 2006; p. 6 47 (Russian original + English translation of relevant parts).
Official Action for Russian Patent Application No. 2013151611 filed Apr. 18, 2012 on behalf of Giovanni Mogna. 12 pages (Russian original + English translation).
PCT International Search Report for PCT/IB2012/000779 filed on Apr. 18, 2012 in the name of Giovanni Mogna. dated Jul. 19, 2012.
PCT Written Opinion for PCT/IB2012/000779 filed on Apr. 18, 2012 in the name of Giovanni Mogna. dated Jul. 19, 2012.
Sgouras Dionyssios N, et al., "Lactobacillus johnsonii La1 attenuates Helicobacter pylori-associated gastritis and reduces levels of proinflammatory chemokines in C57BL/6 mice", Clinical and Diagnostic Laboratory Immunology, American Society for Microbiology, US, vol. 12, No. 12, Dec. 1, 2005, pp. 1378-1386.
Vasiljevic et al., "Probiotics-From Metchnikoff to bioactives", International Dairy Journal, Elsevier Applied Science, Barking, GB, vol. 18, No. 7, Jul. 1, 2008, pp. 714-728, XP022701025.
Wang Kuan-Yuan, et al: "Effects of ingesting Lactobacillus- and Bifidobacterium-containing yogurt in subjects-with colonized Helicobacter pylori", The American Journal of Clinical Nutrition, American Society for Nutrition, US, vol. 80, No. 3, Sep. 1, 2004, pp. 737-741.
Ying, et al: "Microencapsulated Lactobacillus rhamnosus GG Powders: Relationship of Powder Physical Properties to Probiotic Survival during Storage", Journal of Food Science, vol. 75, No. 9, Nov. 1, 2010 (Nov. 1, 2010), pp. E588-E595. Abstract Only.
Shu, Q. et al. FEMS Immunology and Medical Microbiology. 2002, 34, 59-64.
Vicariotto et al. Journal of Clinical Gastroenterology, Nov. 2014, vol. 48, Supp.1, S96-S101.
Terris et al. "Dietary Supplementation with Cranberry Concetnrate Tablets may Increase the Risk of Nephrolithiasis" Urology, 2001, 57(1), pp. 26-29.
Broadbent et al. "Biochemistry, Genetics, and Applications of Exopolysaccharide Production in *Streptococcus thermophiles*: A Review" J. Dairy Sci., 2003, 86, pp. 407-423.
Final Office Action for U.S. Appl. No. 13/982,255, filed Nov. 12, 2013 on behalf of Giovanni Mogna. dated Sep. 17, 2015. 15 pages.
Notice of Allowance for U.S. Appl. No. 13/982,255, filed Nov. 12, 2013 on behalf of Giovanni Mogna. dated Jan. 22, 2016. 10 pages.
Notice of Allowance for U.S. Appl. No. 13/982,255, filed Nov. 12, 2013 on behalf of Giovanni Mogna. dated Jun. 15, 2016. 11 pages.
Notice of Allowance for U.S. Appl. No. 13/982,255, filed Nov. 12, 2013 on behalf of Giovanni Mogna. dated Jul. 27, 2016. 11 pages.
Restriction Requirement for U.S. Appl. No. 14/005,821, filed Nov. 6, 2013 on behalf of Giovanni Mogna. dated Jan. 7, 2014. 7 pages.
Restriction Requirement for U.S. Appl. No. 14/113,211, filed Nov. 26, 2013 on behalf of Giovanni Mogna. dated Sep. 5, 2014. 9 pages.
Non-Final Office Action for U.S. Appl. No. 14/113,211, filed Nov. 26, 2013 on behalf of Giovanni Mogna. dated Apr. 22, 2015. 13 pages.
Non-Final Office Action for U.S. Appl. No. 14/113,211, filed Nov. 26, 2013 on behalf of Giovanni Mogna. dated Jan. 22, 2016. 13 pages.
Non-Final Office Action for U.S. Appl. No. 14/113,211, filed Nov. 26, 2013 on behalf of Giovanni Mogna. dated Nov. 22, 2016. 12 pages.
Final Office Action for U.S. Appl. No. 14/116,999, filed Dec. 20, 2013 on behalf of Giovanni Mogna. dated Dec. 9, 2016. 28 pages.
Restriction Requirement for U.S. Appl. No. 14/344,047, filed Jul. 28, 2014 on behalf of Giovanni Mogna. dated Feb. 19, 2016. 8 pages.
Non-Final Office Action for U.S. Appl. No. 14/344,047, filed Jul. 28, 2014 on behalf of Giovanni Mogna. dated Oct. 13, 2016. 27 pages.
Non-Final Office Action for U.S. Appl. No. 14/344,021, filed Apr. 9, 2014 on behalf of Giovanni Mogna. dated Apr. 18, 2016. 29 pages.
Final Office Action for U.S. Appl. No. 14/344,021, filed Apr. 9, 2014 on behalf of Giovanni Mogna. dated Jan. 31, 2017. 19 pages.
Restriction Requirement for U.S. Appl. No. 14/346,941, filed Mar. 24, 2014 on behalf of Giovanni Mogna. dated Nov. 16, 2016. 8 pages.
Non-Final Office Action for U.S. Appl. No. 14/891,306, filed Nov. 13, 2015 on behalf of Giovanni Mogna. dated Nov. 22, 2016. 37 pages.
Decision to Grant for Russian Patent Application No. 2013148474/15 filed May 9, 2012 on behalf of Probiotical S.P.A. dated May 31, 2017. 15 pages. (Russian Original + 2 pages of English Translation).

\* cited by examiner

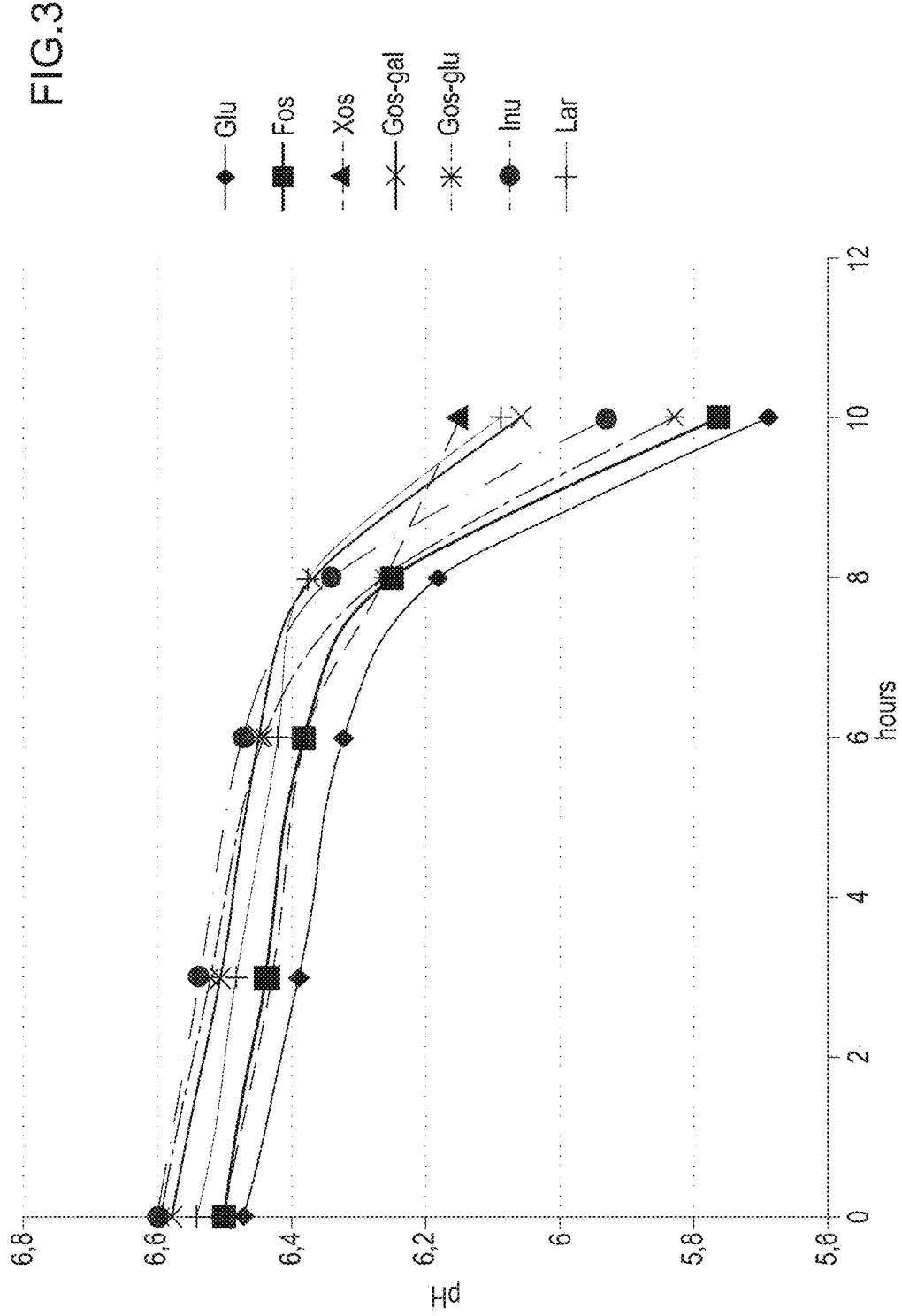

BACTERIAL STRAINS BELONGING TO THE GENUS *BIFIDOBACTERIUM* FOR USE IN THE TREATMENT OF HYPERCHOLESTEROLAEMIA

CROSS REFERENCE TO RELATED APPLICATIONS

The present application is the US national stage of International Patent Application PCT/IB2012/000907 filed on May 9, 2012 which, in turn, claims priority to Italian Patent Application MI2011A000792 filed on May 9, 2011.

The present invention relates to selected bacterial strains belonging to the genus *Bifidobacterium* for use in the treatment of hypercholesterolaemia. In particular, the present invention relates to a food composition or supplement product or medical device or pharmaceutical composition comprising said bacterial strains in association with sterols or phytosterols and/or stanols or phytostanols and/or glucomannan and/or konjac gum and/or prebiotic fibres and/or fermented red rice and/or betaglucans from oats, oat bran, barley, barley bran and/or *aloe arborescens* gel in lyophilized form.

It is well known that all the cells of the body are capable of synthesizing cholesterol from acetyl coenzyme A, but most cholesterol is produced in the peroxisomes of liver cells, which transfer it to the blood so as to be transported throughout the body.

When we speak of "cholesterol" in medicine, we do not mean cholesterol as a chemical product, but are rather actually talking about a class of lipoproteins (chylomicrons, transport aggregates) which circulate in the blood. The concentration of the aforesaid lipoproteins is called blood cholesterol. Depending on their composition in terms of cholesterol, phospholipids, proteins, triglycerides and fatty acids, these aggregates are further distinguished in several classes (according to the specific weight, comprised between 0.98 and 1.17 $g/cm^3$): VLDL (very low density lipoproteins), IDL (intermediate density lipoproteins), LDL (low density lipoproteins), HDL2 and HDL3.

The biosynthesis of cholesterol is regulated by the intracellular concentration of cholesterol and by the hormones insulin and glucagon, so that cholesterol is synthesized only in case of need, to avoid wasting energy. In fact, a high intracellular concentration of cholesterol associated with the hormones insulin and glucagon inhibits the enzyme HMG-CoA reductase, thus blocking the biosynthesis of new cholesterol. For this reason, the amount of cholesterol synthesized is inversely proportional to the amount of cholesterol taken in through the diet.

In the case of a hypercholesterolaemic diet, the amount of cholesterol synthesized through cholesterol biosynthesis decreases, but the cholesterol test parameters can nonetheless exceed the threshold values recommended by the World Health Organization: total blood cholesterol below 200 mg/dl and a total cholesterol/HDL ratio of less than 5 (for men) and less than 4.5 (for women). Approximately, the following are recognized:
i) Normal blood cholesterol levels, with a value of less than 200 mg/dl blood cholesterol.
ii) Mild hypercholesterolaemia, with a value comprised from 200 to 249 mg/dl.
iii) Moderate hypercholesterolaemia, with a value comprised from 250 to 299 mg/dl.
iv) Severe hypercholesterolaemia, with a value greater than 300 mg/dl.

The fact of exceeding the threshold values (200 mg/dl) of the cholesterol test parameters limits many people in the choice of foods they can eat and in the lifestyle they can maintain. These limitations/deprivations can also have consequences on the mood of the people themselves, who view themselves as deprived of the freedom of choosing what to eat since they are conscious of the fact that the choice of eating a dish with a high cholesterol content implies either a series of sacrifices in the following days or, in some cases, a sense of guilt about having "disobeyed" or contributed to increasing the blood cholesterol values.

Therefore, it would be useful and desirable to have a composition capable of normalizing the cholesterol test parameters in subjects who occasionally indulge in high-cholesterol foods.

The existence of drugs, such as statins, which inhibit endogenoous cholesterol synthesis by acting on the enzyme 3-hydroxy-3-methylglutaril-CoA reductase, an enzyme that converts molecules of 3-hydroxy-3-methylglutaril-CoA into mevalonic acid, a precursor of cholesterol, is well known.

A problem deriving from the intake of said drugs, e.g. statins, lies in the fact that by reducing the level of endogenous cholesterol said drugs contribute to increasing the biosynthesis of intracellular cholesterol.

An increase in the biosynthesis of intracellular cholesterol means that when a patient stops taking statins, for example, the biosynthesis of intracellular cholesterol is not immediately normalized (reduced) upon interruption of the intake of the statins, but rather continues as if the patient were still taking the drug (there is said to be a "past memory").

Therefore, once the intake of statins, for example, is interrupted, the biosynthesis of intracellular cholesterol takes a certain amount of time before being normalized, i.e. before reducing said biosynthesis to the levels existing before the intake of the statin-based drug began. This uncontrolled and unnecessary production of cholesterol represents a serious drawback.

Therefore, it would be desirable to have a treatment as an alternative to statins, for example, but not only. The treatment called for must be a treatment that can be freely interrupted by the subject without any further cholesterol production. In practical terms, it would be desirable to have a new treatment which, on the one hand, is capable of reducing the endogenous level of cholesterol and, on the other hand, in the event that the treatment itself is interrupted, is capable of normalizing the biosynthesis of intracellular cholesterol so as to normalize the physiological level of cholesterol.

The Applicant has provided an answer to the above-mentioned needs following an intense activity of research, at the end of which it identified, from a highly vast set of strains, a selection of bacterial strains belonging to the genus *Bifidobacterium*. Said strains exhibit a marked ability to reduce the blood cholesterol level, in particular the level of LDL cholesterol.

BRIEF DESCRIPTION OF THE DRAWINGS

FIG. 3. Determination of acidification curves for the strain *B. bifidum* MB109.

Figure 1:
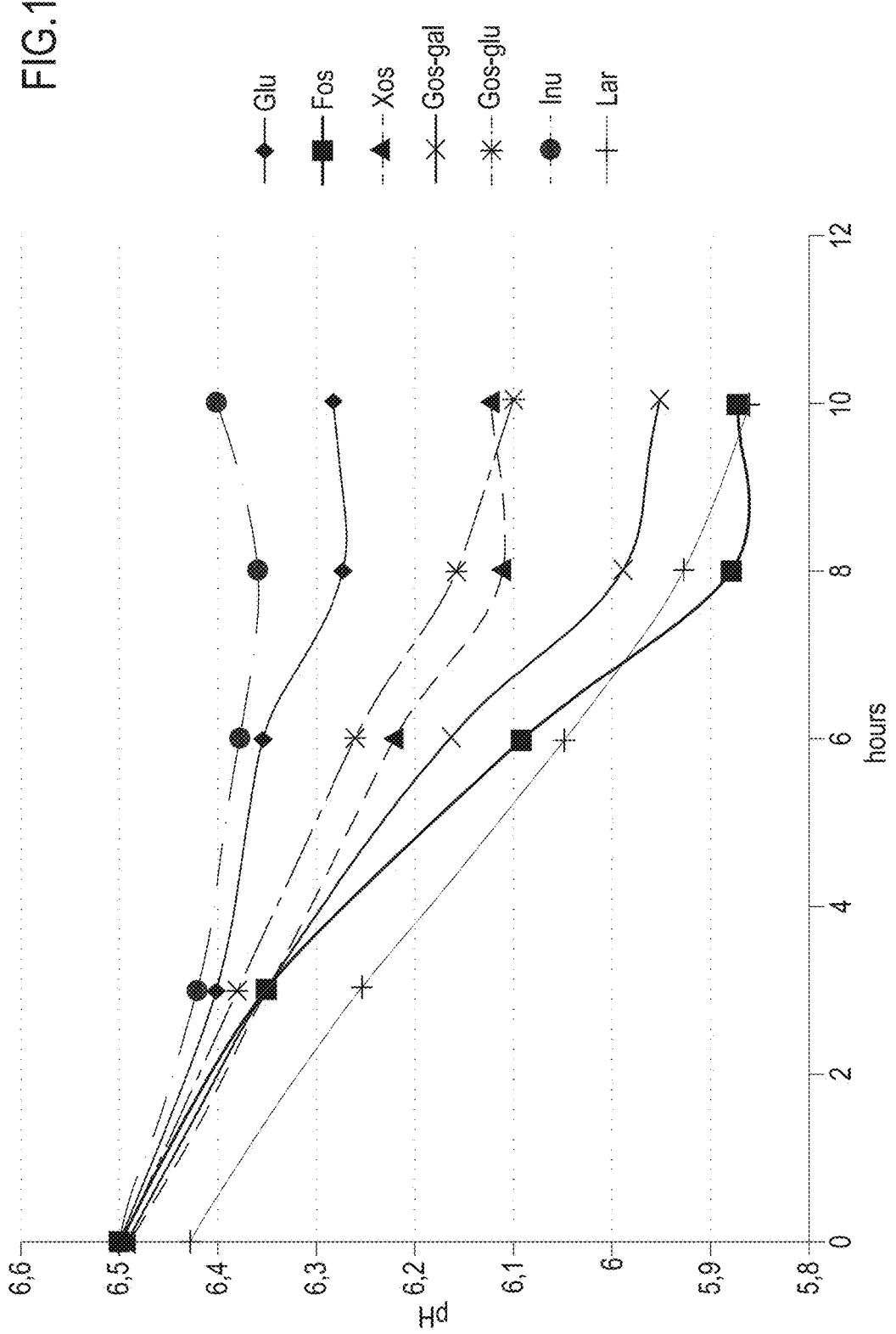
FIG. 1. Determination of acidification curves for the strain *B. longum* BL04 DSM 23233.

The subject matter of the present invention relates to a bacterial strain belonging to the genus *Bifidobacterium* and having the characteristics as disclosed in the appended claim.

Said strain belongs to the species *Bifidobacterium bifidum*. The Applicant carried out a selection on many bacterial strains belonging to the species *Bifidobacterium bifidum*. The strains selected for their properties are:

(i) *Bifidobacterium bifidum* BB06 deposited by the company Probiotical S.p.A of Novara (Italy) with the DSMZ on 29 Mar. 2011, with accession number DSM 24688.

(ii) *Bifidobacterium bifidum* MB109 deposited by the company Probiotical S.p.A of Novara (Italy) with the DSMZ on 29 Jun. 2010, with accession number DSM 23731.

The Applicant carried out a selection on many bacterial strains belonging to the species *Bifidobacterium lactis*. The strains selected for their properties are:

(i) *Bifidobacterium lactis* MB2409 deposited by the company Probiotical S.p.A of Novara (Italy) with the DSMZ on 29 Jun. 2010, with accession number DSM 23733.

(ii) *Bifidobacterium lactis* BS07 (MB243) deposited by the company Probiotical S.p.A of Novara (Italy) with the DSMZ on 29 Mar. 2011, with accession number DSM 24690.

The Applicant carried out a selection on many bacterial strains belonging to the species *Bifidobacterium breve*. The strain selected for its properties is *Bifidobacterium breve* MB113 deposited by the company Probiotical S.p.A of Novara (Italy) with the DSMZ on 29 Jun. 2010, with accession number DSM 23732.

The Applicant carried out a selection on many bacterial strains belonging to the species *Bifidobacterium infantis*. The strain selected for its properties is *Bifidobacterium infantis* BI02 (MB287) deposited by the company Probiotical S.p.A of Novara (Italy) with the DSMZ on 29 Mar. 2011, with accession number DSM 24687.

In the context of the present invention, the bacteria can be present in isolated form or with the respective supernatant. They can be present in the form of live or dead bacteria or components thereof or as a cellular extract or enzymatic extract.

The subject matter of the present invention relates to a food composition or supplement product or medical device or pharmaceutical composition having the characteristics disclosed in the appended claim.

The food composition or supplement product or medical device or pharmaceutical composition comprises a mixture of bacterial strains consisting of at least one bacterial strain belonging to the genus *Bifidobacterium* having the ability to reduce the level of blood cholesterol, in particular LDL cholesterol.

In another preferred embodiment, said at least one bacterial strain is selected from the group comprising the bacterial strains belonging to the species *Bifidobacterium bifidum*, *Bifidobacterium lactis*, *Bifidobacterium breve* and *Bifidobacterium infantis*.

The food composition or supplement product or medical device or pharmaceutical composition comprises a mixture of bacterial strains consisting of at least one bacterial strain selected from the group comprising or, alternatively, consisting of:

(1) *Bifidobacterium bifidum* BB06 (MB107) deposited by the company Probiotical S.p.A of Novara (Italy) with the DSMZ on 29 Mar. 2011, with accession number DSM 24688; and/or (2) *Bifidobacterium bifidum* MB109 deposited by the company Probiotical S.p.A of Novara (Italy) with the DSMZ on 29 Jun. 2010, with accession number DSM 23731; and/or (3) *Bifidobacterium lactis* MB2409 deposited by the company Probiotical S.p.A of Novara (Italy) with the DSMZ on 29 Jun. 2010, with accession number DSM 23733, and/or (4) *Bifidobacterium lactis* BS07 (MB243) deposited by the company Probiotical S.p.A of Novara (Italy) with the DSMZ on 29 Mar. 2011, with accession number DSM 24690; and/or (5) *Bifidobacterium breve* MB113 deposited by the company Probiotical S.p.A of Novara (Italy) with the DSMZ on 29 Jun. 2010, with accession number DSM 23732; and/or (6) *Bifidobacterium infantis* BI02 (MB287) deposited by the company Probiotical S.p.A of Novara (Italy) with the DSMZ on 29 Mar. 2011, with accession number DSM 24687.

The subject matter of the present invention relates to a food composition or supplement product or medical device or pharmaceutical composition which comprises a bacterial composition consisting of (i) at least one bacterial strain belonging to the species *Bifidobacterium bifidum* capable of adsorbing cholesterol onto its surface cell wall, and (ii) at least one bacterial strain belonging to the species *Bifidobacterium lactis*, *Bifidobacterium breve* or *Bifidobacterium infantis* capable of hydrolyzing bile salts at an intracellular and/or extracellular level, for use in the preventive or curative treatment of hypercholesterolaemia.

The food composition or supplement product or medical device or pharmaceutical composition is intended for use to reduce the level of LDL cholesterol in the blood. Moreover, said strain belonging to the species *Bifidobacterium bifidum* is selected from the group consisting of the bacterial strain *B. bifidum* BB06 (MB107) DSM 24688 and the bacterial strain *B. bifidum* (MB109) DSM 23731. Furthermore, said strain belonging to the species *Bifidobacterium lactis* is selected from the group consisting of the bacterial strain *B. lactis* (MB2409) DSM 23733 and the bacterial strain *B. lactis* BS07 (MB243) DSM 24690. Moreover, said strain belonging to the species *Bifidobacterium breve* is the bacterial strain *B. breve* (MB113) DSM 23732. Furthermore, said strain belonging to the species *Bifidobacterium infantis* is the bacterial strain *B. infantis* BI02 (MB287) DSM 24687.

The food composition or supplement product or medical device or pharmaceutical composition further comprises a bacterial strain belonging to the species *Bifidobacterium longum* capable of producing conjugated linoleic acid (CLA) from linoleic acid (LA). Moreover, said strain belonging to the species *Bifidobacterium longum* is *Bifidobacterium longum* (BL04) DSM 23233.

The subject matter of the present invention relates to a food composition or supplement product or medical device or pharmaceutical composition that comprises a bacterial composition consisting of at least one bacterial strain belonging to the species *Bifidobacterium bifidum*, at least one bacterial strain belonging to the species *Bifidobacterium lactis* and at least one bacterial strain belonging to the species *Bifidobacterium longum*, for use in the preventive or curative treatment of the hypercholesterolaemia. Said strain belonging to the species *Bifidobacterium bifidum* is selected from the group consisting of the bacterial strain *B. bifidum* BB06 (MB107) DSM 24688 and the bacterial strain *B. bifidum* (MB109) DSM 23731; preferably it is the bacterial strain *B. bifidum* (MB109) DSM 23731. Moreover, said strain belonging to the species *Bifidobacterium lactis* is selected from the group consisting of the bacterial strain *B. lactis* (MB2409) DSM 23733 and the bacterial strain *B.*

*lactis* BS07 (MB243) DSM 24690; preferably it is the bacterial strain *B. lactis* (MB2409) DSM 23733. Moreover, said strain belonging to the species *Bifidobacterium longum* is *Bifidobacterium longum* (BL04) DSM 23233.

In the food composition or supplement product or medical device or pharmaceutical composition there is further present at least one vegetable substance selected from the group comprising sterols or phytosterols, stanols or phytostanols, glucomannan, konjac gum and/or at least one prebiotic fibre selected from the group comprising fructo-oligosaccharides—FOS, galacto-oligosaccharides—GOS, xylo-oligosaccharides—XOS, inulin, larch fibres or arabinogalactan and/or fermented red rice and/or betaglucans from oats, oat bran, barley, barley bran and/or *aloe arborescens* gel in lyophilized form.

In the food composition or supplement product or medical device or pharmaceutical composition there is further present: (i) at least one vegetable substance selected from the group comprising sterols or phytosterols and/or stanols or phytostanols in association with at least one vegetable substance selected from the group comprising glucomannan, konjac gum, fermented red rice, betaglucans from oats, oat bran, barley, barley bran and *aloe arborescens* gel in lyophilized form;

(ii) at least one vegetable substance selected from the group comprising sterols or phytosterols and/or stanols or phytostanols in association with at least one vegetable substance selected from the group comprising glucomannan, konjac gum, fermented red rice, betaglucans from oats, oat bran, barley, barley bran and *aloe arborescens* gel in lyophilized form in association with at least one prebiotic fibre selected from the group comprising FOS, GOS, XOS, inulin, larch fibre or arabinogalactan.

Advantageously, the food composition or supplement product or medical device or pharmaceutical composition comprises a mixture of bacterial strains comprising or, alternatively, consisting of at least two bacterial strains. At least a first strain must have a mechanism of non-specific adsorption of cholesterol (cholesterol adsorption onto the surface cell wall of the bacterium), whereas at least a second strain must have a specific BSH (Bile Salts Hydrolase) enzymatic activity.

The food composition or supplement product or medical device or pharmaceutical composition of the present invention has valid application in the preventive or curative treatment of disorders or pathologies connected with high blood cholesterol levels, i.e. cholesterol levels exceeding 200 mg/dl; and in the treatment of hypercholesterolaemia.

The above-described compositions, to which the present invention relates, have valid application in reducing the level of blood cholesterol, in particular LDL cholesterol.

In a preferred embodiment, the food composition or supplement product or pharmaceutical composition of the present invention further comprises at least one vegetable substance selected from the group comprising or, alternatively, consisting of sterols or phytosterols and/or stanols or phytostanols. The amount of sterols/stanols per daily dose of composition must be greater than 0.8 g, preferably from 1 g to 3 g, for example, from 1.5 to 2.0 g.

In a preferred embodiment, the food composition or supplement product or medical device or pharmaceutical composition of the present invention further comprises at least one vegetable substance selected from the group comprising or, alternatively, consisting of glucomannan, konjac gum, fermented red rice, betaglucans from oats, oat bran, barley, barley bran and *aloe arborescens* gel in lyophilized form. The amount of glucomannan/konjac gum per daily dose of composition must be greater than 4 g, preferably from 5 g to 10 g, for example, from 6 to 8 g.

If betaglucans from oats, oat bran, barley or barley bran are used, an intake of 3 grams per day must be ensured in order to contribute to maintaining normal blood cholesterol levels.

In a preferred embodiment, the food composition or supplement product or medical device or pharmaceutical composition of the present invention further comprises at least one vegetable substance selected from the group comprising or, alternatively, consisting of sterols and stanols in association with at least one other substance of vegetable origin selected from the group comprising or, alternatively, consisting of glucomannan and konjac gum. The daily recommended doses are indicated above.

In a preferred embodiment, the food composition or supplement product or pharmaceutical composition of the present invention further comprises at least one prebiotic fibre selected from the group comprising or, alternatively, consisting of FOS, GOS, XOS and inulin.

In a preferred embodiment, the food composition or supplement product or pharmaceutical composition of the present invention further comprises at least one vegetable substance selected from the group comprising or, alternatively, consisting of sterols and stanols in association with at least one prebiotic fibre selected from the group comprising or, alternatively, consisting of FOS, GOS, XOS and inulin.

In a preferred embodiment, the food composition or supplement product or pharmaceutical composition of the present invention further comprises at least one vegetable substance selected from the group comprising or, alternatively, consisting of glucomannan and konjac gum in association with at least one prebiotic fibre selected from the group comprising or, alternatively, consisting of FOS, GOS, XOS and inulin.

In a preferred embodiment, the food composition or supplement product or pharmaceutical composition of the present invention further comprises at least one vegetable substance selected from the group comprising or, alternatively, consisting of sterols and stanols in association with at least one vegetable substance selected from the group comprising or, alternatively, consisting of glucomannan and konjac gum in association with at least one prebiotic fibre selected from the group comprising or, alternatively, consisting of FOS, GOS, XOS, inulin.

The above-described compositions have valid application in the treatment of healthy subjects having a blood cholesterol level that is within the normal range, but which occasionally, due to the intake of a quantity of fats in the diet, can increase, giving rise to "temporary" hypercholesterolaemia. In this case, the intake, by these subjects, of a composition according to the present invention can bring the blood cholesterol level back within the normal range, since there is a reduction in excess cholesterol.

Moreover, the above-described compositions also have valid application in the treatment of subjects who normally have a high blood cholesterol level. In this case, the intake, by these subjects, of a composition according to the present invention can limit the increase in the blood cholesterol level.

As shown in the acidification curves that follow, the strain BL04 prefers a vegetable substance such as FOS, larch fibres or arabinogalactan and GOS-Gal, the strain MB2409 prefers a vegetable substance such as FOS and GOS-Galè and the strain MB109 prefers a vegetable substance such as FOS and inulin.

EXPERIMENTAL PART

The Applicant engaged in intense research activity with the aim of selecting the bacterial strains.

In Vivo Study

A total of 32 rats were housed in cages. After several days of acclimatization to the habitual diet (T0), the rats all began to receive the same 100% hypercholesterolemizing diet. After 15 days of this diet (T15), the rats were randomly divided into 4 subgroups (8 rats per subgroup). The rats began receiving differentiated treatments from T15 to T45. These treatments continued for 30 days until sacrifice (T45):

Group 1:

30% hypercholesterolemizing diet and *Lactobacillus reuteri* NCIMB 701359 (Kandler et al.; 1982), $1 \times 10^9$/day (reference). This strain is known for its ability to lower cholesterol levels (reference);

Group 2:

30% hypercholesterolemizing diet and mixture of probiotics [*B. lactis* MB2409 DSM 23733 ($0.33 \times 10^9$/day), *B. breve* MB113 DSM 23732 ($0.33 \times 10^9$/day) and *B. bifidum* MD109 DSM 23731 ($0.33 \times 10^9$/day)];

Group 3:

30% hypercholesterolemizing diet (control).

The daily dose per rat was 1 ml of a suspension containing ($1 \times 10^9$ CFU/ml) of the bacterial strains indicated above. The dose was administered to the rats through a gastric probe.

Blood samples were taken at T0, T15 and T45 after fasting. The serum was separated from the blood obtained and the following serum parameters were determined: a) LDL cholesterol, b) HDL cholesterol, c) total cholesterol and d) triglycerides.

Phases of the Study

Phase I. Normal preliminary diet for all rats for 7 days (T-7).

Phase II. 100% hypercholesterolemizing diet for all rats from day zero (T0) to the fifteenth day (T15).

Phase III. Differentiated diet, as described above, for the 4 groups from the sixteenth to the forty-fifth day (T45).

Experimental Results

1) Change in Body Weight

The first parameter examined was the ponderal growth of the rats in order to verify a correct food intake. The data demonstrate that the rats took in food in a correct manner.

2) Effect of the Hypercholesterolemizing Diet

Since all the rats received the same diet in this first phase, they were all grouped together. Then a comparison was made among the LDL cholesterol, HDL cholesterol, total cholesterol and blood triglyceride levels at time zero (T0) and after 15 days (T15). The HDL/LDL ratio was also calculated, see Table 1.

TABLE 1

| Blood parameters | T0 | T15 |
|---|---|---|
| LDL cholesterol (mg/dl) | 18.52 ± 1.07 | 22.31 ± 3.86° |
| HDL cholesterol (mg/dl) | 65.22 ± 3.10 | 21.85 ± 4.50* |
| HDL/LDL | 3.54 ± 0.25 | 1.00 ± 0.22* |

Statistical analysis was performed with the Student's t-test:
°p < 0.01;
*p < 0.001.

The data provided in Table 1 show that the hypercholesterolemizing diet brought about a significant increase in LDL cholesterol (bad cholesterol) and an even more significant decrease in HDL cholesterol (good cholesterol). The HDL/LDL ratio, which in normal conditions should be greater than 3, was decreased by the hypercholesterolemizing diet.

3) Effect of the Different Treatments (Groups 1-3) on LDL Cholesterol

Treatments 1 and 2 (Groups 1 and 2) brought about a significant reduction in LDL cholesterol (p<0.001) compared to the values at T15. In treatment 3 (Group 3), based only on a 30% hypercholesterolemizing diet, the LDL levels did not change compared to T15.

The amount of cholesterol was reduced through two mechanisms:

i) Mechanism 1: Non-specific cholesterol adsorption (onto the surface cell wall of the bacterium)

ii) Mechanism 2: Specific enzymatic activity of BSH (Bile Salts Hydrolase).

The Applicant carried out screening on a highly vast group of bacteria by evaluating the intracellular activity of BSH.

Practically speaking, each bacterial strain was cultured overnight in MRS culture medium+cysteine, 0.05% weight/volume, and was then centrifuged in order to collect a pellet of cells. This pellet was washed twice with a 0.1 M pH 6 sodium phosphate buffer in order to eliminate the extracellular BSH.

The cells were resuspended in 1 ml of pH 6 sodium phosphate buffer; lysed with glass beads via three 5-minute Vortex cycles at maximum speed at 4° C. and incubated with ice for 10 minutes. At the end of the third cycle, the sample was centrifuged at 13000 rpm for 5 minutes and all cellular debris and macromolecules were precipitated so that the supernatant, which also contains the proteins, could be used.

The supernatant underwent analysis to quantify the total proteins contained in it.

For this purpose, the Lowry method was used to determine the total amount of protein present in the extract. Practically speaking, one milliliter of Lowry reagent is added to 200 microliters of extract, appropriately diluted.

Stock Solutions:

Lowry A: ($Na_2CO_3$ in 0.1 M NaOH (Autoclave),
Lowry B: $CuSO_4$ 1% in $H_2O$ (Sterilize by filtration),
Lowry C: 2% Na—K tartrate tetrahydrate in $H_2O$ (Sterilize by filtration).

Lowry reagent (per 50 ml-50 samples): Lowry A 49 ml+Lowry B 0.5 ml+Lowry C 0.5 ml.

200 μl of appropriately diluted sample+1 ml of Lowry reagent are combined at room temperature. They are left to incubate for 10 minutes at room temperature and then 100 microliters of Folin-Cicalteau reagent diluted 1:1 in water is added. After 30 minutes' incubation, absorbance is measured at 500 nm. The data obtained are interpolated along a regression line with BSA. Then the total protein content of the extract is determined and expressed in mg/ml. The specific activity of BSH is titrated (units of BSH/mg of total protein) so as determine the portion of proteins present in the cellular extract which possesses BSH enzymatic activity.

For this purpose, 20 microliters of a substrate containing taurodeoxycholic acid (TDCA)—TCDA sample—or glycocholic acid (GCA)—GCA sample—is added to the 20 microliters of the above-described extract at a concentration of 200 mM. 360 microliters of 0.1 M pH 6 sodium phosphate buffer is added. The experimental blank is represented by 20 microliters of extract and 380 microliters of 0.1 M pH 6 sodium phosphate buffer—blank sample.

The samples (TDCA sample, GCA sample and blank sample) are incubated at 37° C. This is repeated for the extract obtained from each strain. After 10 and 30 minutes of incubation, 100 microliters of the above-described samples is collected and 100 microliters of TCA (15% trichloroacetic acid) is added to precipitate the proteins. This is followed by 5 minutes' centrifugation at 13000 rpm in order to obtain an acidic mixture and the supernatant, which will contain the amino acids glycine and taurine, is collected.

50 microliters of acidic mixture (for each acidic mixture obtained, i.e. blank sample, TDCA sample and GCA sample) collected at 10 and 30 minutes were analysed as such and diluted 1:5. In detail, the as such samples were evaluated using the ratios of 50 microliters of acidic mixture and 950 microliters of ninhydrin mixture, whereas the 1:5 dilution was evaluated by adding 10 microliters of acidic mixture to 40 microliters of demineralised water and adding 950 microliters of ninhydrin mixture. The ninhydrin mixture was prepared as follows: 2 milliliters of 1% ninhydrin in a 0.5 M pH 5.5 citrate buffer; 4.8 milliliters of glycerol and 0.8 milliliters of 0.5 M pH 5.5 citrate buffer. The samples were boiled for 14 minutes and cooled for 3 minutes in water. The absorbance of each sample was read at 570 nanometers.

Quantifying the taurine and glycine requires a specific calibration curve at a standard concentration of taurine or glycine.

Determination of the Units of BSH Enzymatic Activity per ml of Extract:

U/ml=micromoles of taurine or glycine released per minute/ml=[[Abs 570 of the unknown sample−Abs 570 of the blank]/10 minutes]·1/[(1.25×1000)·(dilution factor 1 or 5)]

The BSH units (U)/ml of extract are converted into BSH units (U)/mg of total proteins based on the total protein concentration determined using the Lowry method.

At the end of this screening carried out on all the strains (by determination of the specific activity of BSH (Lowry and ninhydrin) a further analysis was conducted, consisting in the determination of GCA biotransformation with whole cells, since it represents "an extracellular activity".

Practically speaking, an overnight broth culture in MRS+ 0.05% cysteine weight/volume is carried out and then the OD at 600 nanometers is measured in order to standardize the cellular concentration.

A blank containing MRS+0.05% cysteine is prepared. 20 microliters of a 200 mM solution of glycocholic acid (GCA) is added to 1 ml of each sample; then follows incubation at 37° C. for 20 minutes. Subsequently, 100 microliters is collected and 100 microliters of 15% trichloroacetic acid is added to interrupt the reaction. Then the samples are centrifuged at 12000 rpm for 5 minutes so as to separate the whole cells and proteins; they are diluted 25 times with demineralised water and injected into HPLC-MS to calculate the conversion % compared to the blank sample.

HPLC Operating Conditions:
Column: Zorbax Eclipse,
Flow rate: 0.2 ml/min,
Injection: 1 µl,
$\lambda$=200 nm,
Solvent: A=dd $H_2O$; B=ACN,
Gradient: B % T(min); 10%, 5 min; 100%, 30 min; 100%, 50 min; 10%, 55 min.

Retention time: GCA (MW=464):33.04 min; CA (MW=407):35.41 min

MS (Mass Spectroscopy) Operating Conditions:
Polarity: negative,
Ac. Time: 300,
Capillary current: 3500 V,
Nebulizer: 30 psi,
Dry gas: 8.0 l/min,
Dry temp.: 325° C.,
T(min): 0-30, 30-40, 40-55.

A calculation is made of the conversion %, i.e. of how much CA and GCA is present, in order to determine the presence of extracellular BSH.

Therefore, the 32 initial strains were screened considering the value of intracellular BSH (Lowry method and ninhydrin assay) and bioconversion of GCA into CA—extracellular BSH (HPLC chromatography+MS). see Table 2.

TABLE 2

| Bacterium | % Bioconversion (BSH extracellular activity) | % average GCA bioconversion | average BSH intracellular activity vs. GCA | Std Dev. |
|---|---|---|---|---|
| L. reuteri NCIMB 701359 | 98 | 82.7 | 90.4 | 1.12 | 0.13 |
| B. lactis DSM 24690 | 100 | 100 | 100 | 0.59 | 0.15 |
| B. lactis DSM 23733 | 79.8 | 63.9 | 71.9 | 0.77 | 0.20 |
| B. bifidum DSM 23731 | 64.2 | 71.2 | 67.7 | 0.10 | 0.03 |
| B. breve DSM 23732 | 14.7 | 14.7 | 14.7 | 1.18 | 0.29 |
| B. infantis DSM 24687 | 6.6 | 6.9 | 6.8 | 0.67 | 0.06 |
| B. Bifidum DSM 24688 | — | — | — | 0.15 | 0.07 |

The strains were subsequently tested in order to determine their ability to reduce cholesterol by adsorption.

The cholesterol adsorption capacity was evaluated by culturing the strains in MRS medium+cysteine, to which 100 milligrams/liter of cholesterol was added. The cultures were incubated at 37° C. for 48 hours. At 24 and 48 hours after the start of incubation, samples were taken and the cholesterol remaining in the supernatant was analyzed by HPLC. The cholesterol adsorbed onto the cells was calculated and compared to a non-inoculated control (MRS medium+cysteine+100 mg/l of cholesterol). The % of cholesterol adsorbed was also considered in relation to the optical density of the culture (% of cholesterol adsorbed/OD), as this ratio expresses the cell's ability to adsorb the cholesterol onto its membrane. The cholesterol concentrations of the unknown samples were determined by means of a calibration curve with known cholesterol concentrations (from 0.00 mg/l to 100 mg/l).

HPLC Method
Column: Zorbax Eclipse XBD-C18 rapid resolution HT 4.6×50 mm 1.8 um,
Mobile phase: ACN,
DAD flow: 200 nm,
Rt cholesterol: 4.0 min
Culture Conditions
Medium
Glucose: 20 g/l,
Bacto proteose peptone no. 3, 10 g/l,
Bacto beef extract: 10 g/l, Bacto yeast extract: 5 g/l,
Sodium acetate 5 g/l,
$K_2HPO_3$: 2 g/l,
Ammonium citrate: 2 g/l,
$MgSO_4$: 0.1 g/l,
$MnSO_4$: 0.05 g/l,
Cysteine: 0.5 g/l,
Tween 80—cholesterol mixture
Autoclave at 110° C. for 30 minutes.
Growth Conditions
10% inoculation from overnight culture,
T=37° C.
Anaerobic conditions in gas,
Initial cholesterol 0.08 g/l
Time=18 hours The cholesterol adsorption values are shown in Table 3.

TABLE 3

| Bacterium | OD 1 | OD 2 | % Adsorption 1 | % Adsorption 2 | % Adsorp/OD 1 | % Adsorp/OD 2 | Avg. |
|---|---|---|---|---|---|---|---|
| L. reuteri NCIMB 701359 | 6.5 | 5.5 | 19.1 | 18.5 | 2.9 | 3.4 | 3.1 |
| B. bifidum DSM 24688 | 1.6 | 1.5 | 55.9 | 43.5 | 34.4 | 29.9 | 32.2 |
| B. bifidum DSM 23731 | 2.3 | 3.4 | 49.4 | 46.9 | 21.1 | 14.0 | 20.1 |
| B. lactis DSM 23733 | 2.7 | 2.2 | 18.6 | 17.7 | 6.8 | 8.2 | 7.5 |
| B. breve DSM 23732 | 1.0 | 1.3 | 6.9 | 8.9 | 7.3 | 6.6 | 7.0 |
| B. infantis DSM 24687 | 10.4 | 9.8 | 32.9 | 28.1 | 3.2 | 2.9 | 3.0 |
| B. lactis DSM 24690 | 2.1 | 2.2 | 18.4 | 13.0 | 8.8 | 6.0 | 7.4 |

The strain B. bifidum BB06 (MB107) DSM 24688 and the strain B. bifidum MB109 DSM 23731 show a high cholesterol adsorption capacity. These two strains absorb a large amount compared to the reference L. reuteri NCIMB 701359.

In a preferred embodiment, the composition of the present invention comprises or, alternatively, consists of at least one strain having a high cholesterol adsorption capacity, selected from the group comprising or, alternatively consisting of B. bifidum BB06 (MB107) DSM 24688 and B. bifidum MB109 DSM 23731, which show a high cholesterol adsorption capacity, in association with at least one strain having an intracellular and/or extracellular BSH activity, selected from the group comprising or, alternatively, consisting of B. lactis MB2409 DSM 23733, B. breve MB113 DSM 23732, B. infantis B102 (MB287) DSM 24687 and B. lactis BS07 (MB243) DSM 24690. Said composition can further comprise sterols and/or stanols and/or glucomannan and/or konjac gum and/or prebiotic fibres, as described above.

In a preferred embodiment, the composition of the present invention comprises or, alternatively, consists of at least one strain having a high cholesterol adsorption capacity, selected from the group comprising or, alternatively consisting of B. bifidum BB06 (MB107) DSM 24688 and B. bifidum MB109 DSM 23731, which show a high cholesterol adsorption capacity, in association with at least one strain having a BSH intracellular and/or extracellular activity, selected from the group comprising or, alternatively, consisting of B. lactis MB2409 DSM 23733 (intracellular and extracellular activity of BSH) and B. breve MB113 DSM 23732 (high intracellular activity of BSH). Advantageously, said composition comprises the strain B. bifidum MB109 DSM 23731 in association with B. lactis MB2409 DSM 23733. Said composition can further comprise sterols and/or stanols and/or glucomannan and/or konjac gum and/or prebiotic fibres, as described above.

In a preferred embodiment, the composition comprises, or alternatively consists of, B. bifidum MB109 DSM 23731 in association with B. lactic MB2409 DSM 23733. Said composition can further comprise sterols and/or stanols and/or glucomannan and/or konjac gum and/or prebiotic fibres, as described above.

The above-described compositions, to which the present invention relates, have valid application for reducing the level of blood cholesterol, in particular LDL cholesterol.

The above-described compositions, to which the present invention relates, have valid application in the preventive or curative treatment of disorders or pathologies connected with high blood cholesterol levels, cholesterol levels above 200 mg/dl; and in the treatment of hypercholesterolaemia.

Clinical Study

A clinical effectiveness study was conducted using a placebo tablet containing fructo-oligosaccharides (FOS) and silicon dioxide (total powder/capsule=280.6 mg) and a tablet containing B. lactis ME 2409 DSM23733, B. bifidum MB 109 DSM 23731 and B. longum BL 04 DSM 23233 and silicon dioxide (total powder/capsule=280.6 mg).

Substantially, two strains with hypocholesterolemizing activity and the strain that best converted linoleic acid (LA) into conjugated linoleic acid (CLA) were combined.

Type of study: double-blind randomized crossover versus placebo. The crossover was planned to take place after 75 days (15 days with 2 capsules/day+60 days with 1 capsule/day). The total duration of the study was 150 days. Load guaranteed at the end of the period: 1 billion/strain/capsule.

The dosage provided for in the study for each treatment (active or placebo) was the following: 2 capsules/day for the first 15 days, 1 capsule/day for the next 60 days; after the crossover, again 2 capsules/day for the first 15 days, 1 capsule/day for the next 60 days. The clinical study confirmed the effectiveness of the tested bacterial composition in reducing the blood cholesterol level by as much as 25%.

Figure 2:
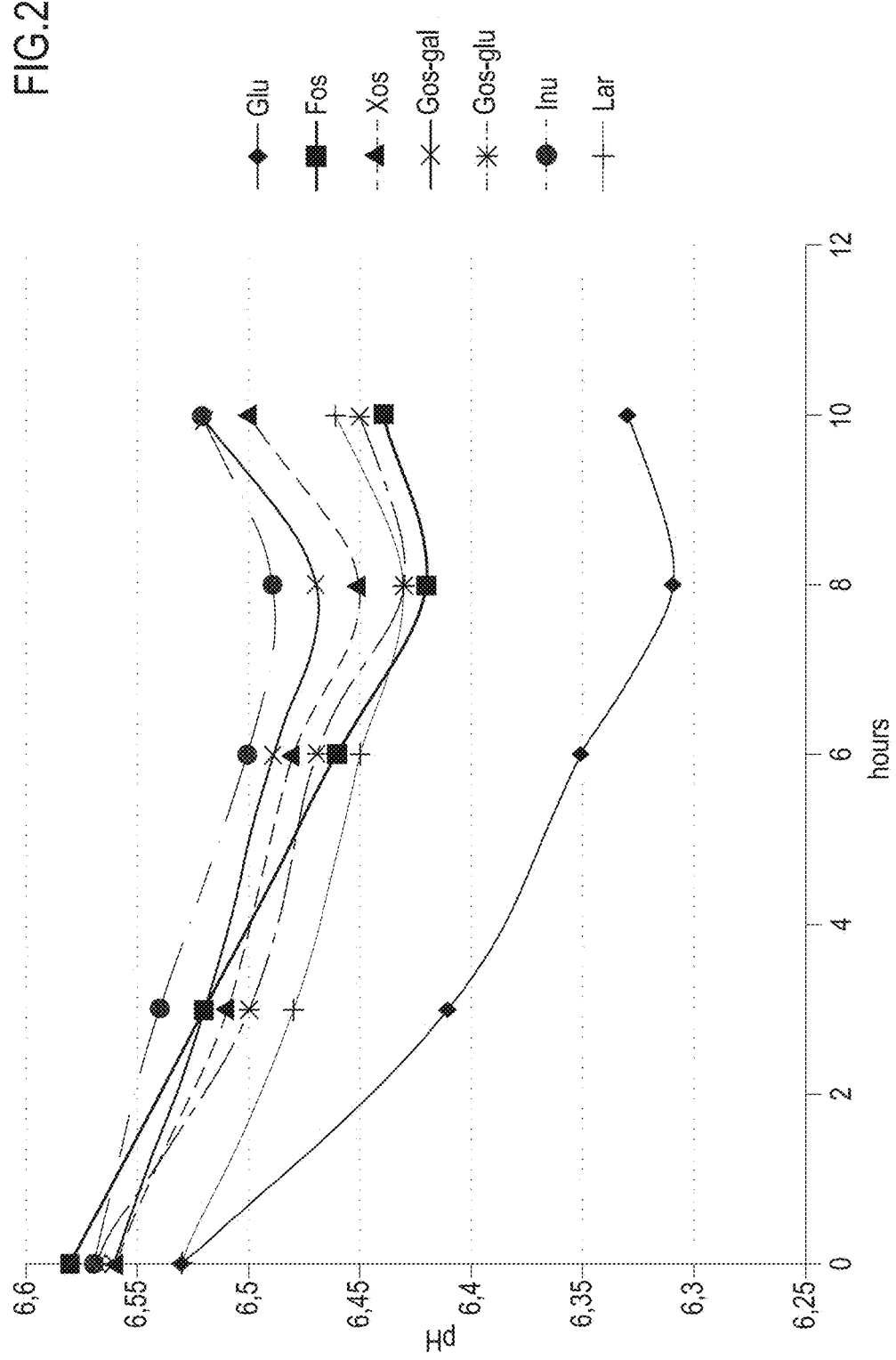
FIG. 2. Determination of acidification curves for the strain *B. lactis* MB2409 DSM 23733.

Determination of Acidification Curves for the Strains B. bifidum MB109 DSM 23731, B. lactis MB2409 DSM 23733 and B. longum BL04 DSM 23233 (Tables 4, 5, 6 and FIGS. 1, 2, 3).

The strains MB109, MB2409 and BL04 were reactivated before the experiment by subculture in TPY+1% Cys-HCl and incubated under anaerobiosis at 37° C. The reactivation steps were repeated three times before the experiment with overnight incubation. At the end of the third reactivation step the cells were pelleted, washed with sterile water and resuspended prior to inoculation into the fibre-supplemented media. The media used are based on sugar-free MRS (carbon sources) supplemented respectively with:

Glucose (solution sterilized by heat treatment, 121° C. 15'), control medium.
FOS (solution sterilized by filtration, 0.20 μl filter).
GOS-Glu—Galacto-oligosaccharides with glucose residue (solution sterilized by filtration, 0.20 μl filter).
GOS-Gal—Galacto-oligosaccharides with galactose residue (solution sterilized by filtration, 0.20 μl filter).
XOS (solution sterilized by filtration, 0.20 μl filter).

Larex—larch fibre or arabinogalactan (solution sterilized by heat treatment, 121° C. 15').

Inulin (solution sterilized by heat treatment, 121° C. 15').

The final concentration of carbon sources for all media was 20 g/l. The media thus composed were then inoculated with 4% of the strains MB109, MB2409 and BL04 (with the addition of 1% Cys-HCl) and incubated at 37° C. under aerobiosis. At time 0 and at 3, 6, 8 and 10 hours the pH values were measured in order to construct the acidification curves shown in the graphs.

TABLE 4

|  |  | 0 | 3 | 6 | 8 | 10 |
|---|---|---|---|---|---|---|
| BL04 | Glu | 6.5 | 6.4 | 6.35 | 6.27 | 6.28 |
|  | Fos | 6.5 | 6.35 | 6.09 | 5.88 | 5.87 |
|  | Xos | 6.49 | 6.35 | 6.22 | 6.11 | 6.12 |
|  | Gos-gal | 6.49 | 6.35 | 6.16 | 5.99 | 5.95 |
|  | Gos-glu | 6.5 | 6.38 | 6.26 | 6.16 | 6.1 |
|  | Inu | 6.5 | 6.42 | 6.38 | 6.36 | 6.4 |
|  | Lar | 6.43 | 6.25 | 6.05 | 5.92 | 5.86 |

TABLE 5

|  |  | 0 | 3 | 6 | 8 | 10 |
|---|---|---|---|---|---|---|
| MB2409 | Glu | 6.53 | 6.41 | 6.35 | 6.31 | 6.33 |
|  | Fos | 6.58 | 6.52 | 6.46 | 6.42 | 6.44 |
|  | Xos | 6.56 | 6.51 | 6.48 | 6.45 | 6.5 |
|  | Gos-gal | 6.56 | 6.52 | 6.49 | 6.47 | 6.52 |
|  | Gos-glu | 6.57 | 6.5 | 6.47 | 6.43 | 6.45 |
|  | Inu | 6.57 | 6.54 | 6.5 | 6.49 | 6.52 |
|  | Lar | 6.53 | 6.48 | 6.45 | 6.43 | 6.46 |
|  |  | 0 | 3 | 6 | 8 | 10 |

TABLE 6

|  |  | 0 | 3 | 6 | 8 | 10 |
|---|---|---|---|---|---|---|
| MB109 | Glu | 6.47 | 6.39 | 6.32 | 6.18 | 5.69 |
|  | Fos | 6.5 | 6.44 | 6.38 | 6.25 | 5.76 |
|  | Xos | 6.5 | 6.43 | 6.38 | 6.26 | 6.15 |
|  | Gos-gal | 6.58 | 6.51 | 6.45 | 6.37 | 6.06 |
|  | Gos-glu | 6.6 | 6.52 | 6.44 | 6.26 | 5.83 |
|  | Inu | 6.6 | 6.54 | 6.47 | 6.34 | 5.93 |
|  | Lar | 6.54 | 6.48 | 6.42 | 6.37 | 6.09 |

The invention claimed is:

1. A method for preventive or curative treatment of hypercholesterolaemia, the method comprising:
   administering to a subject having hypercholesterolaemia or at a risk of developing hypercholesterolaemia a food composition or supplement product or medical device or pharmaceutical composition comprising a bacterial composition comprising:
   at least one bacterial strain belonging to the species Bifidobacterium bifidum capable of absorbing cholesterol onto its surface cell wall, selected from the group consisting of bacterial strain B. bifidum BB06 (MB107) DSM 24688 and bacterial strain B. bifidum MB109 DSM 23731, and
   at least one bacterial strain belonging to the species Bifidobacterium lactis, Bifidobacterium breve or Bifidobacterium infantis capable of hydrolyzing bile salts on an intracellular and/or extracellular level,
   the bacterial composition in an effective amount for preventive or curative treatment of hypercholesterolaemia in the subject.

2. The method according to claim 1, for reducing the level of LDL cholesterol in the blood.

3. The method according to claim 1, wherein said at least one bacterial strain belonging to the species Bifidobacterium bifidum is the bacterial strain B. bifidum MB109 DSM 23731.

4. The method according to claim 1, wherein said at least one bacterial strain belonging to the species Bifidobacterium lactis is selected from the group consisting of the bacterial strain B. lactis MB2409 DSM 23733 and the bacterial strain B. lactis BS07 (MB243) DSM 24690.

5. The method according to claim 1, wherein said at least one bacterial strain belonging to the species Bifidobacterium breve is the bacterial strain B. breve (MB113) DSM 23732.

6. The method according to claim 1, wherein said at least one bacterial strain belonging to the species Bifidobacterium infantis is the bacterial strain B. infantis BI02 (MB287) DSM 24687.

7. The method according to claim 1, the bacterial composition further comprising a bacterial strain belonging to the species Bifidobacterium longum capable of producing conjugated linoleic acid (CLA) from linoleic acid (LA).

8. The method according to claim 7, wherein said bacterial strain belonging to the species Bifidobacterium longum is Bifidobacterium longum BL04 DSM 23233.

9. The method according to claim 7, wherein said bacterial composition consists of at least one of bacterial strain B. bifidum BB06 (MB107) DSM 24688 and bacterial strain B. bifidum MB109 DSM 23731, at least one bacterial strain belonging to the species Bifidobacterium lactis and at least one bacterial strain belonging to the species Bifidobacterium longum.

10. The method according to claim 9, wherein:
   said at least one bacterial strain belonging to the species Bifidobacterium lactis is selected from the group consisting of the bacterial strain B. lactis MB2409 DSM 23733 and the bacterial strain B. lactis BS07 (MB243) DSM 24690; and
   said at least one bacterial strain belonging to the species Bifidobacterium longum is Bifidobacterium longum BL04 DSM 23233.

11. The method according to claim 1, wherein the food composition or supplement product or medical device or pharmaceutical composition further comprises:
   at least a first vegetable substance selected from the group consisting of sterols, phytosterols, stanols, phytostanols, glucomannan, and konjac gum,
   at least one prebiotic fibre selected from the group comprising fructo-oligosaccharides—FOS, galacto-oligosaccharides—GOS, xylo-oligosaccharides—XOS, inulin, larch fibre and arabinogalactan, and
   at least a second vegetable substance selected from the group consisting of fermented red rice, betaglucans from oats, oat bran, barley, barley bran, and aloe arborescens gel in lyophilized form.

12. The method according to claim 1, wherein the food composition or supplement product or medical device or pharmaceutical composition further comprises:
   at least a first vegetable substance selected from the group consisting of sterols, phytosterols, stanols, and phytostanols in association with at least one vegetable substance selected from the group comprising glucomannan, konjac gum, fermented red rice, betaglucans from oats, oat bran, barley, barley bran and aloe arborescens gel in lyophilized form; and
   at least a second vegetable substance selected from the group consisting of sterols, phytosterols, stanols, and phytostanols in association with at least one vegetable substance selected from the group comprising glucomannan, konjac gum, fermented red rice, betaglucans from oats, oat bran, barley, barley bran and *aloe arborescens* gel in lyophilized form in association with at least one prebiotic fibre selected from the group comprising FOS, GOS, XOS, inulin, larch fibre and arabinogalactan.

* * * * *